(12) United States Patent
Shimoe et al.

(10) Patent No.: US 6,454,753 B1
(45) Date of Patent: Sep. 24, 2002

(54) DISPOSABLE DIAPER PROVIDED WITH TAPE FASTENERS

(75) Inventors: Nariaki Shimoe; Kazuaki Onishi, both of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/294,434

(22) Filed: Apr. 20, 1999

(30) Foreign Application Priority Data

Apr. 20, 1998 (JP) .......................................... 10-109689

(51) Int. Cl.$^7$ ................................................ A61F 13/15
(52) U.S. Cl. ................................... 604/391; 604/385.01
(58) Field of Search ................................. 604/391, 390, 604/389, 393, 385.01, 386; 156/765

(56) References Cited

U.S. PATENT DOCUMENTS

| | | | | |
|---|---|---|---|---|
| 3,897,783 A | * | 8/1975 | Ginocchio | 128/290 |
| 4,936,840 A | * | 6/1990 | Proxmire | 604/385.2 |
| 5,399,219 A | * | 3/1995 | Roessler et al. | 156/259 |
| 5,549,592 A | | 8/1996 | Fries et al. | |
| 5,605,735 A | * | 2/1997 | Zehner et al. | 428/100 |
| 5,669,901 A | * | 9/1997 | LaFortune et al. | 604/391 |
| 5,672,404 A | * | 9/1997 | Callahan et al. | 428/100 |
| 5,851,205 A | * | 12/1998 | Hisada et al. | 604/390 |
| 6,030,373 A | * | 2/2000 | VanGompel et al. | 604/386 |
| 6,045,543 A | * | 4/2000 | Pozniak et al. | 604/385.1 |
| 6,099,516 A | * | 8/2000 | Pozniak et al. | 604/386 |
| 6,221,483 B1 | * | 4/2001 | Hilston et al. | 428/343 |

FOREIGN PATENT DOCUMENTS

EP  0 486 006 A2 A3  5/1992

OTHER PUBLICATIONS (1) European Search Report and Annex.

* cited by examiner

Primary Examiner—Aaron J. Lewis
Assistant Examiner—Michael Bogart
(74) Attorney, Agent, or Firm—Lowe Hauptman Gilman & Berner, LLP

(57) ABSTRACT

A disposable diaper includes tape fasteners each having an elastically stretchable/contractile basic tape member and a hook member attached onto an inner surface of the basic tape member. The hook member has inner and outer side edges, and the inner side edge extends towards a proximal end portion of the basic tape member in its transversely middle zone.

21 Claims, 4 Drawing Sheets

DISPOSABLE DIAPER PROVIDED WITH TAPE FASTENERS

BACKGROUND OF THE INVENTION

The present invention relates to disposable diapers provided with tape fasteners used when the diaper is put on a wearer's body.

Conventional disposable diapers are provided with tape fasteners laterally extending from transversely opposite side edges of a rear waist region of the diaper so that the tape fasteners may be separably anchored on a front waist region of the diaper when the diaper is put on a wearer's body. A specific example of such a tape fastener comprises a basic tape member which is elastically stretchable and contractile circumferentially of the diaper. An end of the basic tape member on a side of the diaper is joined to a corresponding side edge of the diaper and an end of the basic tape member remote from the diaper carries thereon a hook member as one component of mechanical fasteners. To put the diaper on the wearer's body, the basic tape member is longitudinally stretched until said hook member can be engaged with a loop member attached to the front waist region :as the other component of the mechanical fastener. In general, the hook member is of a rectangular shape.

With such elastic tape fastener, its basic tape member and possibly the hook member carried thereon tend to be transversely curved away from the diaper as said tape fastener is stretched in a direction of waist-line in order to anchor the tape fastener to the front waist region. If the hook member also is curved together with the basic tape member, the hook member will be curved away from the surface of the loop member to be engage the hook member and make reliable engagement with the loop member difficult. In other words, an effective surface area of the hook member will become substantially smaller than its actual surface area. As a result, a desired high fastening effect can not be obtained even if the hook member of a relatively large size is employed.

SUMMARY OF THE INVENTION

In view of the problem as has been pointed out, it is an object of the present invention to utilize an available surface area of the hook member attached to the elastic tape fastener as efficiently as possible.

According to the invention, there is provided a disposable diaper comprising a liquid-pervious topsheet, a liquid-impervious backsheet and a liquid-absorbent core disposed between the topsheet and the backsheet, longitudinally opposite ends extending in parallel to each other in a direction of waist-line and transversely opposite side edges extending in parallel to each other, a pair of tape fasteners extending outwards from the side edges, respectively, in the direction of waist-line, wherein: each of the tape fasteners has a basic tape member which is elastically stretchable/contractile in the direction of waist-line and a hook member; the basic tape member has a longitudinal direction extending in parallel to the direction of waist-line and a transverse direction being orthogonal to the direction of waist-line, the basic tape member including, in the longitudinal direction, a proximal end portion joined to one of the side edges of the diaper and a distal end portion opposed to the proximal end portion, and the hook member is attached to the basic tape member on an inner surface of the distal end portion so as to be spaced from the proximal end portion and has inner and outer side edges extending transversely of the basic tape member, and the inner side edge extends towards the proximal end portion in a transversely middle zone of the basic tape member.

DETAILED DESCRIPTION OF THE PREFERRED EMBODIMENTS

Details of a disposable diaper provided with a tape fasteners according to the present invention will be more fully understood from the description given hereunder with reference to the accompanying drawings.

Figure 1:
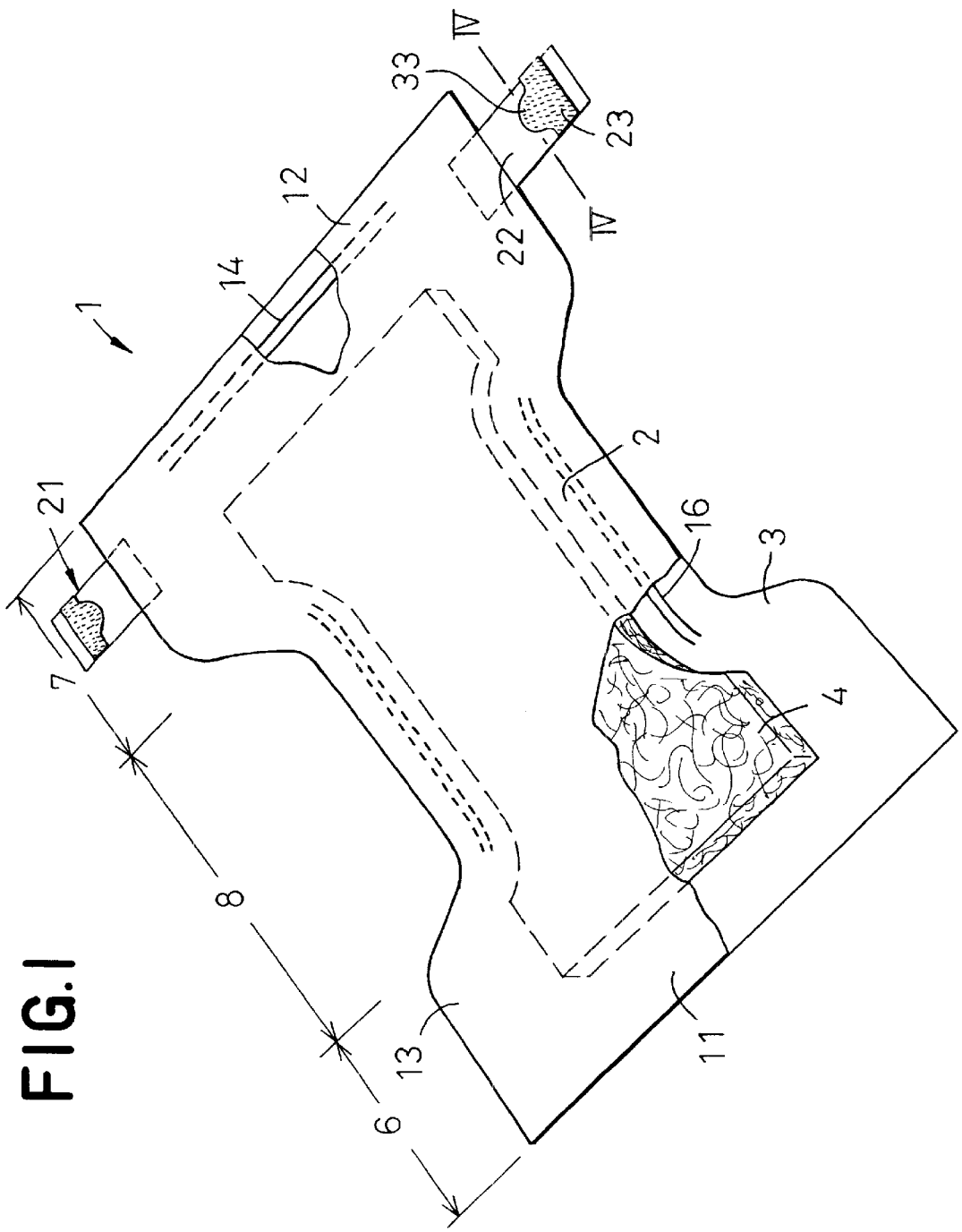
FIG. 1 is a perspective view showing a disposable diaper arranged according to one embodiment of the present invention as partially broken away.

Disposable diaper 1 provided with tape fasteners shown by FIG. 1 in a perspective view as partially broken away comprises a liquid-pervious topsheet, a liquid-impervious backsheet and a liquid-absorbent core 4 disposed between the topsheet 2 and the backsheet 3. Configurationally, the diaper 1 has a front waist region 6, a rear waist region 7 and a crotch region 8 extending between the front and rear waist regions 6, 7.

The topsheet 2 and the backsheet 3 are placed upon each other and bonded together over their portions extending outwards beyond a peripheral edge of the core 4 so as to define longitudinally opposite ends 11, 12 extending in a direction of waist-line and transversely opposite side edges 13, 13 extending transversely of said ends 11, 12. The rear end 12 and the side edges 13, 13 are respectively provided with an elastic member 14 associated with a waist-opening and elastic members 16, 16 associated with a pair of leg-openings. The elastic members 14, 16, 16 are disposed between the topsheet 2 and the backsheet 3 and bonded under appropriate tension to an inner surface of at least one of the topsheet 2 and the backsheet 3. A pair of tape fasteners 21, 21 extending laterally from the side edges 13, 13, respectively. The fasteners 21 may be separably anchored to an outer surface of the front waist region 6 when the diaper 1 is put on the wearer's body.

Figure 2:
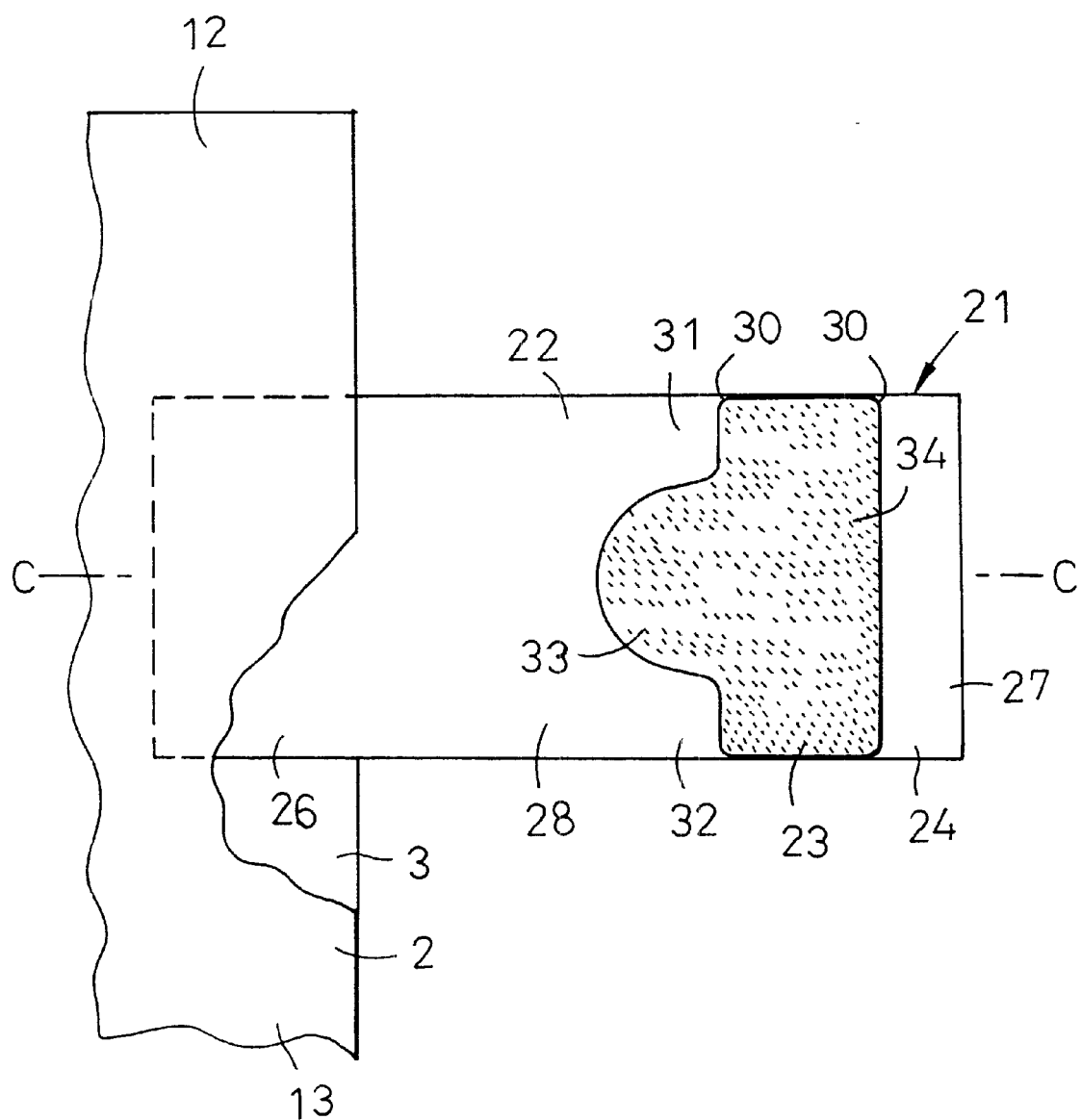
FIG. 2 is a diagram showing a part of FIG. 1 in an enlarged scale.
Figure 3:
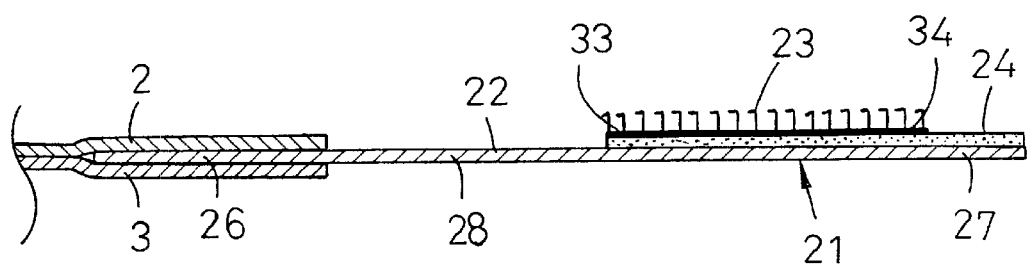
FIGS. 3 and 5 are sectional views taken along line C—C in FIG. 2 in accordance with two embodiments of the present invention.

FIG. 2 is a fragmentary plan view showing details of the tape fastener 21 and FIG. 3 is a sectional view taken along center line C—C dividing the fastener 21 in upper and lower halves as viewed in FIG. 2. The fastener 21 comprises a basic tape member 22 being elastically stretchable/contractile in the direction of waist-line, a hook member 23 forming a part of the known mechanical fasteners which further includes a loop member as a counterpart, and an inelastic sheet member 24.

The basic tape member 22 has a longitudinal direction which is parallel to the direction of waist-line and a transverse direction which is orthogonal to the direction of waist-line. The basic tape member 22 extends from its proximal end portion 26 joined to at least one of the topsheet 2 and the backsheet 3 to its distal end portion 27 opposed to the proximal end portion 26. The basic tape member 22 has an elastically stretchable/contractile zone 28 adjacent the side edge 13 and upper and lower edges 31, 32 extending in parallel to each other in the direction of waist-line.

The hook member 23 is attached to an inner surface of the basic tape member 22 slightly spaced inwards from the distal end portion 27 so as to extend between the upper and lower edges 31, 32. The hook member 23 has an inner edge 33 adjacent the proximal end portion 26 of the basic tape member 22 and an outer edge 34 remote from the proximal end portion 26. The inner edge 33 describes, in vicinity of the center line C—C, a curve which extends towards the proximal end portion 26 relative to the remaining zones adjacent the upper and lower edges 31, 32, respectively. The zone 28 in which the basic tape member 22 is elastically stretchable/contractile in the direction of waist-line is defined between the inner edge 33 and the proximal end portion 26. According to this specific embodiment, the outer edge 34 extends transversely of the basic tape member 22 substantially in a vertical direction as viewed in FIG. 2.

The inelastic sheet member 24 is disposed between the basic tape member 22 and the hook member 23 in. the direction of fastener's thickness and partially covers the inner. surface of the distal end portion 27. The sheet member 24 has its inner edge lying in coincidence with the inner edge of the hook member 23 and its outer edge extending outwards beyond the outer edge of the hook member 23 to the distal end portion 27 of the basic tape member 22 so as to be placed thereupon with a same shape as the distal end portion 27. The inelastic sheet member 24 partially rigidifies the distal end portion 27 of the basic tape member 22 and thereby facilitates the hook member 23 to be anchored to the loop member (not shown) on the front waist region 6. Additionally, the sheet member 24 makes an outermost region of the distal end portion 27 inelastic and thereby facilitates the tape fastener 21 to be held between the wearer's or helper's fingers of a wearer or an assisting person. It should be understood that the present invention can be exploited also without use of such inelastic sheet member 24 if the above-mentioned functions and/or effects provided by the inelastic sheet member 24 are not required for the tape fastener 21.

Figure 4:
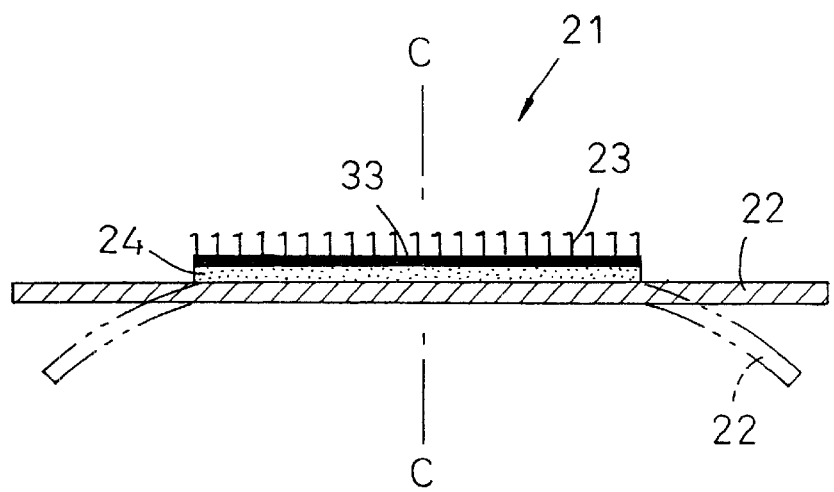
FIG. 4 is a sectional view taken along a line IV—IV in FIG. 1.

FIG. 4 is a sectional view taken along line IV-IV in FIG. 1. As represented by imaginary lines, the basic tape member 22 is curved outwardly of the diaper 1 as the flat tape fastener 21 is stretched in the direction. of waist-line. However, the hook member 23 is substantially free from affection of the basic tape member 22 being curved in such a manner and remains flat, because the inner edge 33 of the hook member 23 is present only in proximity of the center line C—C.

Figure 5:
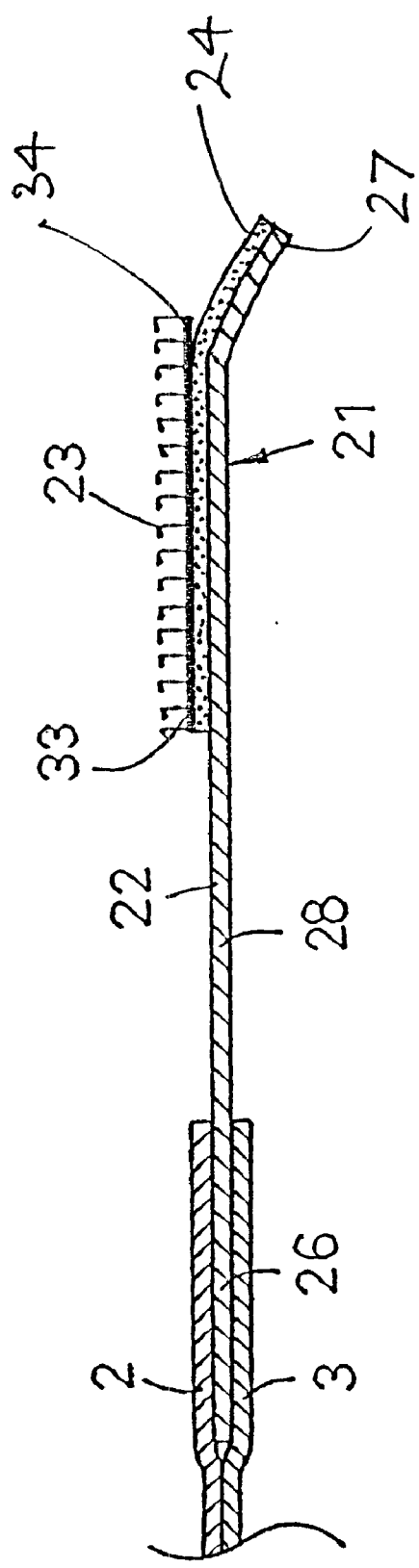

With the tape fastener 21 for the disposable diaper as has been described hereinabove, the hook member 23 is shaped so that most of its surface area is concentrated in vicinity of the center line C—C. Such an arrangement is advantageous in that, even if the elastic basic tape member 22 is stretched in the direction of waist-line and consequently curved transversely away from the diaper 1 as shown in FIG. 4, the hook member 23 can be maintained flat over most of its surface area and easily as well as accurately anchored to the loop member. The hook member 23 is preferably arranged so that 60–80% of its surface area is present in ranges of 25% of a full width of the tape fastener 21 above and below of the center line C—C, respectively. Corners 30 (See FIG. 2) of the hook member 23 preferably describe circular arcs with a radius of 0.5~5 mm in order that these corners 30 should not stimulate the wearer's skin. While the hook member 23 as a whole is preferably laminated with the basic tape member 22 as in the embodiment shown in FIG. 3, it is also possible to laminate the inner edge 33 and the zone in vicinity thereof with the basic tape member 22 leaving the outer edge 34 free, as in the embodiment shown in FIG. 5, if it is unnecessary to laminate the hook member 23 entirely with the basic tape member 22.

To assemble the diaper 1, joining or bonding of the respective members may be achieved using an adhesive agent such as hot melt adhesive or glue. For the members made of heat-sealable materials, it is also possible to utilize the heat-sealing technique for the joining or bonding.

The disposable diaper according to the present invention allows the hook member to be easily and accurately anchored to the loop member even if the elastically stretchable/contractile fastener is transversely curved away from the diaper as the fastener is stretched in the direction of waist-line. This is achieved by the unique arrangement of the hook member such that its inner edge extends towards the proximal end portion of the fastener in vicinity of the transversely middle zone of the fastener.

What is claimed is:

1. A disposable diaper, comprising:
   a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and
   a pair of tape fasteners extending outwards from transversely opposite side edges of said basic diaper structure, respectively, in said waist circumferential direction;
   each of said tape fasteners consisting essentially of a single hook member attached to a basic tape member which is elastically stretchable/contractile in said waist circumferential direction;
   said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and
   said hook member being attached to said basic tape member on an inner surface of said distal end portion so as to be spaced apart from said proximal end portion and having inner and outer side edges extending transversely of said basic tape member, and said inner side edge extends towards said proximal end portion in a transversely middle zone of said basic tape member;
   wherein an inelastic sheet member is disposed between said basic tape member and said hook member and covers the inner surface of said distal end portion.

2. The disposable diaper according to claim 1, wherein said inelastic sheet member rigidifies a region of said tape fastener where said hook member is attached to said basic tape member.

3. The disposable diaper according to claim 1, wherein a rigidity of said tape fastener in an entire region between the outer side edge of said hook member and an outermost edge of said basic tape member is lower than in a region where said hook member is attached to said basic tape member.

4. The disposable diaper according to claim 3, wherein the inelastic sheet member is distinct from said hook member.

5. The disposable diaper according to claim 3, wherein the outer side edge of said hook member is substantially straight.

6. The disposable diaper according to claim 5, wherein a distance between the outer side edge of said hook member and an outermost edge of said basic tape member is shorter than a distance between the inner side edge of said hook member and said proximal end portion of said basic tape member.

7. The disposable diaper according to claim 3, wherein a distance between the outer side edge of said hook member and an outermost edge of said basic tape member is shorter than a distance between the inner side edge of said hook member and said proximal end portion of said basic tape member.

8. A disposable diaper, comprising:
- a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and
- a pair of tape fasteners extending outwards from transversely opposite side edges of said basic diaper structure, respectively, in said waist circumferential direction;
- each of said tape fasteners having a basic tape member which is elastically stretchable/contractile in said waist circumferential direction and a single hook member;
- said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and
- said hook member being attached to said basic tape member on an inner surface of said distal end portion so as to be spaced apart from said proximal end portion and having inner and outer side edges extending transversely of said basic tape member, and said inner side edge extends towards said proximal end portion in a transversely middle zone of said basic tape member; wherein
  - an inelastic sheet member is disposed between said basic tape member and said hook member and covers the inner surface of said distal end portion;
  - a rigidity of said tape fastener in an entire region between the outer side edge of said hook member and an outermost edge of said basic tape member is lower than in a region where said hook member is attached to said basic tape member; and
  - said inelastic sheet member makes the outermost region of said distal end portion, defined between an outer edge of said basic tape member and the outer edge of said hook member, inelastic.

9. The disposable diaper according to claim 1, wherein the inelastic sheet member is distinct from said hook member.

10. The disposable diaper according to claim 1, wherein the outer side edge of said hook member is substantially straight.

11. The disposable diaper according to claim 10, wherein a distance between the outer side edge of said hook member and an outermost edge of said basic tape member is shorter than a distance between the inner side edge of said hook member and said proximal end portion of said basic tape member.

12. A disposable diaper, comprising:
- a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and
- a pair of separately formed tape fasteners being bonded to and extending outwards from transversely opposite side edges of said basic diaper structure, respectively, in said waist circumferential direction;
- each of said tape fasteners having a basic tape member which is elastically stretchable/contractile in said waist circumferential direction and a-hook member;
- said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and
- said hook member being attached to said basic tape member on an inner surface of said distal end portion so as to be spaced apart from both said proximal end portion and an outermost edge of said basic tape member, said hook member having inner and outer side edges extending transversely of said basic tape member, said inner side edge extending towards said proximal end portion in a transversely middle zone of said basic tape member;
- wherein an inelastic sheet member is disposed between said basic tape member and said hook member and extends beyond the outer side edge of said hook member to the outermost edge of said basic tape member.

13. The disposable diaper according to claim 12, wherein the inelastic sheet member is distinct from said hook member.

14. The disposable diaper according to claim 12, wherein a distance between the outer side edge of said hook member and the outermost edge of said basic tape member is shorter than a distance between the inner side edge of said hook member and said proximal end portion of said basic tape member.

15. The disposable diaper according to claim 12, wherein the inelastic sheet member has an inner side edge lying in coincidence with the inner side edge of said hook member, and an outer side edge lying in coincidence with the outermost edge of said basic tape member.

16. The disposable diaper according to claim 12, wherein the said hook member further having two parallel side edges connecting the inner and outer side edges thereof, corners defined by each of the two parallel side edges and one of the inner and outer side edges are radiussed.

17. A disposable diaper, comprising:
- a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and
- a pair of tape fasteners extending outwards from transversely opposite side edges of said basic diaper structure, respectively, in said waist circumferential direction;
- each of said tape fasteners having a basic tape member which is elastically stretchable/contractile in said waist circumferential direction and a single hook member;
- said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and said hook member being attached to said basic tape member on an inner surface of said distal end portion so as to be spaced apart from said proximal end portion and having inner and outer side edges extending transversely of said basic tape member, and said inner side edge extends towards said proximal end portion in a transversely middle zone of said basic tape member;

wherein
an inelastic sheet member is disposed between said basic tape member and said hook member and covers the inner surface of said distal end portion;

the outer side edge of said hook member is substantially straight;

a distance between the outer side edge of said hook member and an outermost edge of said basic tape member is shorter than a distance between the inner side edge of said hook member and said proximal end portion of said basic tape member; and a rigidity of said tape fastener in an entire region between the outer side edge of said hook member and the outermost edge of said basic tape member is lower than in a region where said hook member is attached to said basic tape member, but higher than in a region between the inner edge of said hook member and said proximal end portion of said basic tape member.

18. A disposable diaper, comprising:
a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and a pair of separately formed tape fasteners being bonded to and extending outwards from transversely opposite side edges of said basic diaper structure, respectively, in said waist circumferential direction;

each of said tape fasteners having a basic tape member which is elastically stretchable/contractible in said waist circumferential direction and a hook member;

said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and said hook member being attached to said basic tape member on an inner surface of said distal end portion so as to be spaced apart from said proximal end portion and having inner and outer side edges extending transversely of said basic tape member, said inner side edge extending towards said proximal end portion in a transversely middle zone of said basic tape member;

wherein
an inelastic sheet member is disposed between said basic tape member and said hook member and extends to an outermost edge of said basic tape member; and said hook member is configured so that from about 60% to about 80% of an entire area thereof is presented in the transversely middle zone of said basic tape member, the transversely middle zone being defined by two lines extending parallel with and on opposite sides of a center line of said basic tape member, each of the two lines being spaced from the center line by about 25% of a full width of said basic tape basic tape member as measured in the transverse direction thereof.

19. A disposable diaper, comprising:
a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and a pair of tape fasteners extending outwards from transversely opposite side edges of said basic diaper structure, respectively, in said waist circumferential direction;

each of said tape fasteners having a basic tape member which is elastically stretchable/contractible in said waist circumferential direction and a single hook member;

said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and said hook member being attached to said basic tape member on an inner surface of said distal end portion so as to be spaced apart from said proximal end portion and having inner and outer side edges extending transversely of said basic tape member, and said inner side edge extends towards said proximal end portion in a transversely middle zone of said basic tape member;

wherein
an inelastic sheet member is disposed between said basic tape member and said hook member and covers the inner surface of said distal end portion; and said hook member is configured so that from about 60% to about 80% of an entire area thereof is presented in the transversely middle zone of said basic tape member, the transversely middle zone being defined by two lines extending parallel with and on opposite sides of a center line of said basic tape member, each of the two lines being spaced from the center line by about 25% of a full width of said basic tape basic tape member as measured in the transverse direction thereof.

20. A disposable diaper, comprising:
a basic diaper structure comprising a liquid-pervious topsheet, a liquid-impervious backsheet, and a liquid-absorbent core disposed between said topsheet and said backsheet, longitudinally opposite ends of said basic diaper structure extending parallel to each other in a waist circumferential direction of the diaper; and a pair of tape fasteners being bonded to and extending outwards from transversely opposite side edges of said basic diaper structure, respectively, in said waist circumferential direction;

each of said tape fasteners having a basic tape member which is elastically stretchable/contractible in said waist circumferential direction and a hook member;

said basic tape member having a longitudinal direction extending parallel to said waist circumferential direction and a transverse direction being orthogonal to said waist circumferential direction, said basic tape member having in said waist circumferential direction, a proximal end portion joined to one of the side edges of said diaper and a distal end portion opposed to said proximal end portion; and said hook member being attached to said basic tape member on an inner surface of said distal end portion so as to be spaced apart from said proximal end portion and having inner and outer side edges extending transversely of said basic tape member, and said inner side edge extends towards said proximal end portion in a transversely middle zone of said basic tape member;

wherein the inner side edge of said hook member is laminated with said basic tape member while the outer side edge of said hook member is left substantially free of bonding to said basic tape member.

21. The disposable diaper according to claim 1, wherein the outer side edge of said hook member is spaced apart from the outermost edge of said basic tape member and the inelastic sheet member extends beyond the outer side edge of said hook member to the outermost edge of said basic tape member.

* * * * *